United States Patent [19]

Davies et al.

[11] Patent Number: 5,506,266
[45] Date of Patent: Apr. 9, 1996

[54] HYDROXAMIC ACIDS FOR REPERFUSION INJURY

[75] Inventors: Michael J. Davies, Burnholme; Catherine A. Rice-Evans, London, both of England

[73] Assignee: British Technology Group Limited, London, England

[21] Appl. No.: 64,151

[22] PCT Filed: Nov. 15, 1991

[86] PCT No.: PCT/GB91/02017

§ 371 Date: May 17, 1993

§ 102(e) Date: Aug. 30, 1993

[87] PCT Pub. No.: WO92/08453

PCT Pub. Date: May 29, 1992

[30] Foreign Application Priority Data

Nov. 15, 1990 [GB] United Kingdom ............. 9024820

[51] Int. Cl.$^6$ ............................................. A61K 31/19
[52] U.S. Cl. ................................................ 514/575
[58] Field of Search ..................................... 514/575

[56] References Cited

U.S. PATENT DOCUMENTS

| 4,604,407 | 8/1986 | Haslanger et al. | 514/575 |
| 5,187,192 | 2/1993 | Brooks et al. | 514/575 |

FOREIGN PATENT DOCUMENTS

| 0273451 | 6/1988 | European Pat. Off. . |
| 0284645 | 10/1988 | European Pat. Off. . |
| 0365210 | 4/1990 | European Pat. Off. . |

OTHER PUBLICATIONS

C. Rice-Evans et al "The Suppression of Iron Release . . . " Free Radical Res. Commun. vol. 7 No. 1, 1989 Harwood–Acad. Pub. (GB), pp. 45–54.

B. Ramesh Reddy et al "Early Treatment with Deferoxamine . . . " Free Radical Biol. & Medicine vol. 7 No. 1, 1989, Pergamon Press (US), pp. 45–52.

C. G. Pitt et al "The selection and evaluation of new . . . " The Jour. of Pharmacology & Experimental Thera. vol. 208 No. 1, 1979(US), pp. 12–18.

Fu-Chih Huang et al "Differential effects of a Series . . . " J. Med. Chem., vol. 32 No. 8, 1989, Am. Chem. Soc., pp. 1836–1842.

N. V. Konstantinova et al "Herbicide derivatives of . . . " Chemical Abstracts, vol. 70 No. 1 (6 Jan. 1969), Columbus, Ohio, USA, pp. 1583–1589.

Anders et al Leukemia Research 1985 9 463–469, Inhibition of Proleferation and . . .

Hinjosa et al: Photochem & Photo Biol 1989 49 1–5. Electron Spin Resonance Study of the . . .

Primary Examiner—Raymond Henley, III
Assistant Examiner—Kevin E. Weddington
Attorney, Agent, or Firm—Nixon & Vanderhye

[57] ABSTRACT

Compounds of formula (I)

$$R-C(=O)-N(R')-OH \quad (I)$$

in which R and R' are each separately selected from aliphatic hydrocarbon groups, aryl groups and aliphatic hydrocarbon groups substituted by an aryl group, are of value for use in medicaments for the control of free radical induced damage arising from reperfusion injury in tissue, particularly heart damage.

10 Claims, 4 Drawing Sheets

HYDROXAMIC ACIDS FOR REPERFUSION INJURY

This invention relates to the control of free radical induced damage which arises from reperfusion injury to tissues and in particular to the control of heart damage.

BACKGROUND OF THE INVENTION

Damage to the fabric of the heart is one of the commonest causes of human morbidity and mortality. The most usual mode of treatment for patients who have suffered a myocardial infarction is simply the administration of thrombolytic agents. However, in reperfusion injury, although the tissue damage is dependent on the duration of anoxia, the damage is believed to be exacerbated by the sudden perfusion of oxygen leading to the generation of various free radical species. Although many studies have implicated the involvement of free radical species in the cellular damage observed in myocardial reperfusion injury as well as reperfusion injury to other tissues, their nature, source and location nevertheless remain controversial.

Investigations on isolated heart preparations with coronary artery ligation have shown that the incorporation of hydroxyl radical scavengers and desferrioxamine prior to reperfusion decreases the incidence of heart arrhythmias and other markers of radical-mediated damage on reperfusion, such work being discussed by Rice-Evans et al, Free Rad. Res. Comm., 1989, 7, 49. The role of desferrioxamine in limiting myocardial ischaemic/reperfusion injury has also been confirmed by Reddy et al, Free Rad. Biol. Med., 1989, 7, 45, using experiments in dogs.

DESCRIPTION OF THE INVENTION

We have now found, however, that certain other hydroxamate compounds exhibit a much superior effect to desferrioxamine in the control of heart damage resulting from free radical induced damage arising from reperfusion injury.

Accordingly the present invention comprises the use of a compound of formula (I)

in which R and R' are each separately selected from aliphatic hydrocarbon groups, aryl groups and aliphatic hydrocarbon groups substituted by an aryl group, in the manufacture of a medicament, for the control of free radical induced damage arising from reperfusion injury in tissue.

Certain compounds of formula (I) are described for use as intermediates for the preparation of herbicidal compounds as described in U.S. Pat. No. 4,507,148, U.S. Pat. No. 4,604,407 discloses novel hydroxamate compounds, including compounds of formula (I), which inhibit the enzyme lipoxygenase and as such are useful as anti-allergy agents. European Patent Application 0 365 210 discloses hydroxamic acid derivatives, including in particular compounds of formula (I) in which R is methyl, n-propyl or phenyl and R' is undecyl, which are also lipoxygenase inhibitors and indicated to be useful in the treatment of bronchial asthma, allergies, inflammatory diseases and ischaemic heart disorders. European Patent Application 0 273 451 discloses hydroxamate compounds, including compounds of formula (I), which are also lipoxygenase inhibitors, and are indicated to prevent the formation of certain mediators which are implicated in certain inflammatory and allergic disease states. Inhibition of lipoxygenase and prevention of the formation of such mediators as a result alleviates the inflammatory and allergic conditions resulting therefrom.

However, we are not aware of any previous indication in the literature of the compounds of formula (I) being used in the treatment and prevention of reperfusion injury.

As indicated, the compounds (I) contain groups R and R' which are separately selected from aliphatic hydrocarbon groups, aryl groups and aliphatic hydrocarbon groups substituted by an aryl group. The term aliphatic hydrocarbon group is used herein in relation to both the unsubstituted and the substituted groups to include both acyclic and cyclic groups which may be unsaturated or saturated, the acyclic groups having a branched chain or especially a straight chain. Preferred unsubstituted groups are those of up to 8, 10 or 12 carbon atoms, particularly of 1 to 6 carbon atoms for the acyclic groups and 3 to 6 carbon atoms for the cyclic groups, for example acyclic groups of 1, 2, 3, 4, 5 or 6 carbon atoms, and cyclic groups of 3, 4, 5 or 6 carbon atoms. Whilst the cyclic aliphatic hydrocarbon groups are preferably saturated, for example being cyclopropyl or cyclohexyl, both saturated and unsaturated groups are of interest in the case of the acyclic groups, for example allyl, propargyl, methyl, ethyl, propyl, butyl, pentyl and hexyl, the last four terms being used herein to include both the branched and the straight chain groups, although the latter are in general of greater interest.

As regards the substituted aliphatic hydrocarbon groups, these may be selected as just described for the unsubstituted groups, although there is a stronger preference for the smaller groups, particularly those of 1 to 6 carbon atoms for the acyclic hydrocarbon groups and 3 to 6 carbon atoms for the cyclic hydrocarbon groups, and especially those of 1, 2, 3 or 4 and 3 or 4 carbon atoms respectively. The preference is for saturated groups and conveniently also for acyclic groups, aralkyl groups being of particular interest. A further preference is for straight chain groups, and for terminally substituted groups. Substituted $C_{1-6}$ alkyl groups are thus of particular interest, especially substituted ethyl and especially substituted methyl groups since there is a preference for the total size of the aliphatic hydrocarbon group substituted by an aryl group to be up to 8 or 10 carbon atoms.

The term aryl group is used herein in its usual sense, i.e. to indicate an aromatic hydrocarbon group and, as such, includes particularly a 1- or 2-naphthyl group or especially a phenyl group, which groups may optionally be substituted by one or more aliphatic hydrocarbon groups. These substituent groups may conveniently be aliphatic hydrocarbon groups such as those described hereinbefore, particularly $C_{1-4}$ alkyl groups and especially methyl or ethyl. The aryl groups, whether being an aryl group R or R' or part of a group R or R' which is an aliphatic hydrocarbon group susbtituted by an aryl group, are preferably of up to 8 or 10 carbon atoms, particularly of 6 to 8 carbon atoms.

Specific examples of aryl groups and aliphatic groups substituted by an aryl group are phenyl, tolyl, benzyl, α-methylbenzyl and phenethyl.

In general the preferred compounds (I) contain a group R' which is an aliphatic hydrocarbon group and conveniently the group R is also an aliphatic hydrocarbon group. Thus compounds (I) of especial interest contain two $C_{1-12}$ aliphatic hydrocarbon groups, particularly two $C_{1-5}$ or $C_{1-6}$ alkyl groups, for example $C_1$, $C_2$, $C_3$, $C_4$, $C_5$ or $C_6$ alkyl groups. Thus R and R' may particularly each be separately selected from methyl, ethyl, propyl, butyl, pentyl and hexyl. As regards the ease of synthesis of the compounds, in particular, there is a preference where larger groups are present in the compounds (I), whether these are aliphatic hydrocarbon groups, aryl groups or aliphatic hydrocarbon groups substituted by an aryl group, for R to be such a group, since in general R' is preferably ethyl or especially methyl. Examples of specific compounds (I) are N-methyl-acetohydroxamic acid (R=R'=CH$_3$), N-ethyl-acetohydroxamic acid (R=CH$_3$, R'=C$_2$H$_5$), N-methylpropionohydroxamic acid (R=C$_2$H$_5$, R'=CH$_3$) and N-ethylpropionohydroxamic acid (R=R'=C$_2$H$_5$), and their analogues in which R' is methyl and R is propyl, butyl, pentyl, hexyl, phenyl or benzyl and in which R' is ethyl and R is propyl, butyl, pentyl, hexyl, phenyl or benzyl. The most preferred compound is however N-methyl-hexanohydroxamic acid (R$_1$=CH$_3$, R=C$_5$H$_{11}$) which has been shown to have superior properties to its analogues in which R'=CH$_3$ and R is CH$_3$, n-C$_3$H$_7$, n-C$_9$H$_{19}$ and C$_6$H$_5$.

The invention also includes those among the compounds (I) which are novel per se and also the use in therapy of those compounds which are not novel per se but have not been described in the context of a therapeutic use.

If desired the compounds (I) may be used in the form of a physiologically acceptable salt thereof. In particular, these may be formed with various bases. Examples of suitable bases are the alkali metal hydroxides, for example sodium hydroxide, quaternary ammonium hydroxides and amines such as tris (tris representing 2-amino-2-hydroxymethylpropane 1,3-diol). The compounds (I) are, however, only weak acids and in general, therefore, the free acid is of rather greater interest than the salts.

The compounds (I) are readily prepared by reaction of an appropriate compound RCOX in which X is a suitable leaving group, particularly a halogeno group so that RCOX is an acid halide, for example an acid chloride RCOCl, with the appropriate N-substituted hydroxylamine, R'NHOH, in a suitable solvent, for example methanol. A reaction time of 30 minutes and a temperature of 0°–5° C. are often appropriate.

A suitable process for the preparation of a novel compound of formula (I)

(I)

in which R and R' are each separately selected from aliphatic hydrocarbon groups, aryl groups and aliphatic hydrocarbon groups substituted by an aryl group thus comprises reacting an N-substituted hydroxylamine of formula R'NHOH in which R' is as for the compound (I) with a compound of formula RCOX in which R is as for the compound (I) and X is a suitable leaving group, and optionally forming a physiologically acceptable salt thereof.

Without commitment to any specific mode of action of the compounds (I) it may be stated that when used in the control of reperfusion damage following a myocardial infarction they are believed to function through their effect on the elevated levels of free radical species including ferrylmyoglobin present in the body following the infarction. It is believed that this is one of the free radical generating species, which is derived from myoglobin by interaction with oxidising agents such as hydrogen peroxide derived from superoxide radicals generated from cellular sources, and one of the major sources of free radicals arising in reperfusion injury, and plays an important contributory role in the occurrence of heart damage or reperfusion. The compounds (I) are believed to exert their effect both through the inhibition of the oxidation of myoglobin to ferrylmyoglobin and through the reduction of ferrylmyoglobin which has already been formed. Because compounds (I) are believed to be antioxidants, they can additionally act as scavengers of other potential reactive radical species which may arise.

The compounds of formula (I) are, however, not only of value in the treatment of patients who have experienced a myocardial infarction to control reperfusion injury on the sudden supply of oxygen to the heart tissue, but also in the control of reperfusion damage in general or re-supply of oxygen to tissue. Thus the compounds of formula (I) are of interest for use in the control of reperfusion injury to the brain following a stroke. Another specific example of use of the invention is in organ transplant operations, for example of the heart, kidney or liver, where the introduction of the donor transplant organ into the recipient body results in a sudden perfusion of oxygen to the organ on the re-administration of the blood supply which may, if not treated, lead to reperfusion injury due to free radical species being formed.

The compounds (I) may be formulated with a physiologically acceptable diluent or carrier for use as pharmaceuticals for veterinary, especially in a mammalian context, and particularly for human use by a variety of methods. For instance, they may be applied as a composition incorporating a liquid diluent or carrier, for example an aqueous or oily solution, suspension or emulsion, which may often be employed for parenteral administration as an injection or infusion and therefore may conveniently be sterile and pyrogen free. Oral administration may also be used, but the need for as rapid an onset of action as possible in the control of reperfusion injury means that this route is less preferred. Although compositions for oral administration may incorporate a liquid diluent or carrier, it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection, infusion or through the oral route may also be considered in both human and veterinary contexts but are again of less interest than administration by injection or infusion. Such alternative forms include the use of suppositories or pessaries and of compositions for buccal or nasal administration, for example lozenges, nose drops or an aerosol spray.

Thus, the invention further includes the use of a compound (I) as described hereinbefore where the medicament is in injectable or infusable form.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition and the condition being treated, it may be stated by way of guidance that treatment following a myocardial infarction will often utilise a dosage of about 10 to 90 mg/kg, repeated as appropriate, i.e. usually daily but often more frequently immediately after the myocardial infarction and similar doses will usually be appropriate in other contexts. Veterinary doses are broadly similar. However, it will be appreciated that it may be appropriate under certain circumstances to give dosages of the compounds (I) either below or above these levels.

Where desired, more than one compound (I) may be administered in the pharmaceutical composition (usually at a total dosage level as indicated hereinbefore) or, indeed, other active compounds may be included in the composition. In particular, when treating a myocardial infarction or occlusion, thrombolytic agents are commonly administered, usually by infusion, and it is convenient to administer the compounds (I) at the same time. If desired, therefore, such an agent may be incorporated into the composition as an additional active component thereof. Examples of specific thrombolytic agents are streptokinase, urokinase and tissue plasminogen activator (now used as the recombinant material).

The invention therefore further includes a method for the treatment of a patient for the control of reperfusion damage to tissue, for example in the control of damage to the heart following a myocardial infarction, which comprises administering to said patient a therapeutically effective amount of a compound (I) as defined hereinbefore.

When the invention is used in conjunction with organ transplantation it may also be appropriate to incorporate a compound or compounds (I) in the medium in which the organ is stored, for example at a concentration of between 10 and 50 mM as well as in the pre-transplantation refluxing or rinsing solution. In the case of a storage medium, the medium will commonly comprise recommended nutrients as in clinically approved solutions such as high potassium, low sodium with citrate or lactobionate. In addition it is necessary in kidney and liver transplants to reflux the organ before transplantation with a rinse solution. It is therefore beneficial to incorporate a compound or compounds (I) in the rinse solution.

BRIEF DESCRIPTION OF THE DRAWINGS

The invention is illustrated by the following Examples and the accompanying drawings, in which.

EXAMPLES

Figure 1:
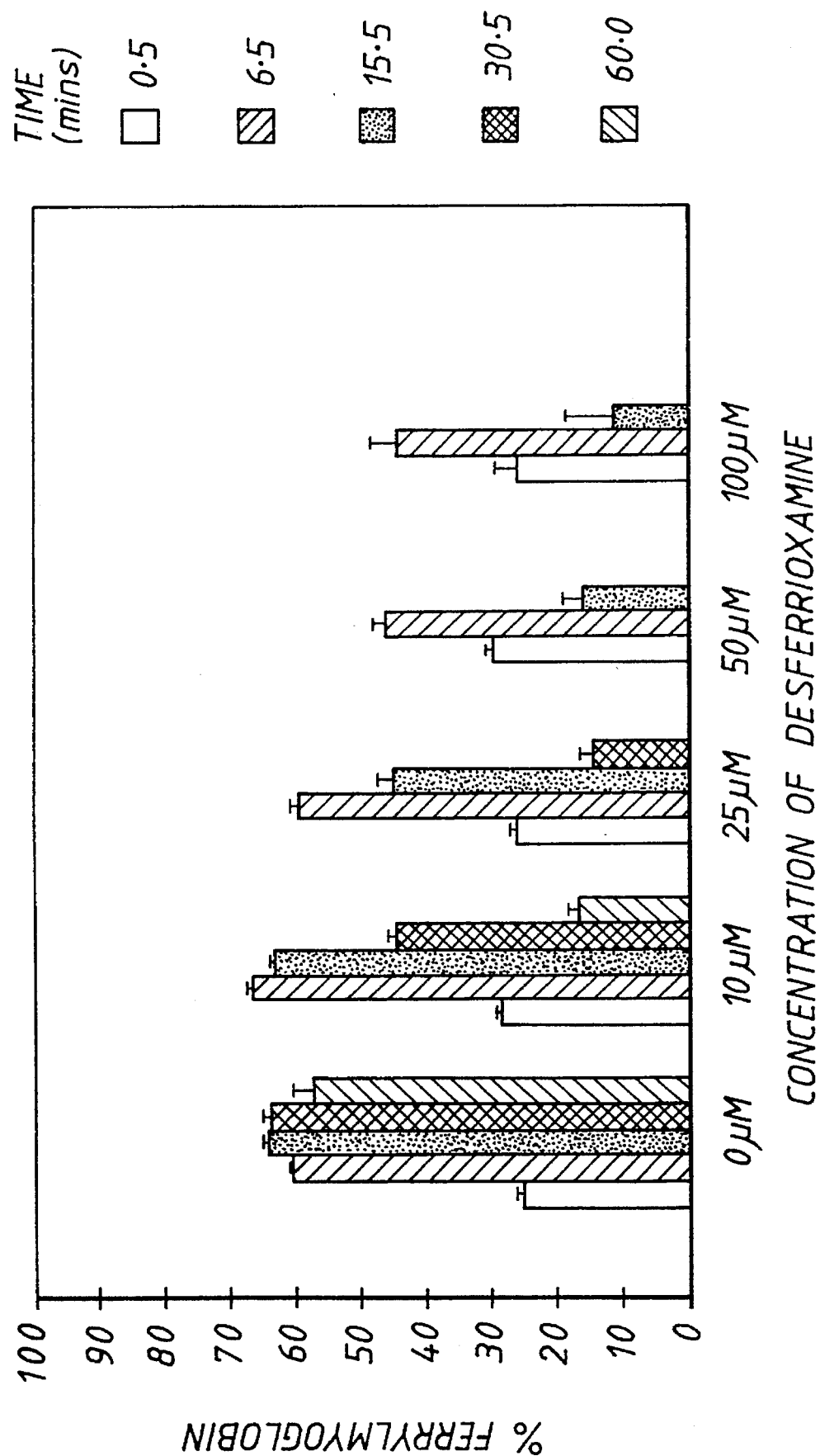
FIGS. 1 through 4 are histograms showing the results obtained in the experiments described in Example 4.

Example 1: Preparation of N-methyl-acetohydroxamic acid (This procedure is based on that of Ulrich et al, J. Chem. Soc., 1963, 1098–1101.)

Acetylchloride (7.85 g, 0.1 mole) is added dropwise with stirring and ice-cooling to a mixture of sodium carbonate (10.6 g, 0.1 mole) and N-methylhydroxylamine hydrochloride (8.35 g, 0.1 mole) in methanol (60 ml), the temperature being kept at less than 5° C. After stirring for a further 30 minutes the mixture is filtered and the solvent is removed using a rotary evaporator. The resultant residue is re-filtered and the residue distilled in vacuo to yield N-methyl-acetohydroxamic acid as an oil, b.p. 74°–76°/0.8 mm.

Example 2: Preparation of N-methyl-hexanohydroxamic acid (This procedure is based on that of Ulrich et al., J. Chem. Soc., 1963, 1098–1101.)

Hexanoylchloride ( g, 0.1 mole) is added dropwise with stirring and ice-cooling to a mixture of sodium carbonate (10.6 g, 0.1 mole) and N-methylhydroxylamine hydrochloride (8.35 g, 0.1 mole) in methanol (60 ml), the temperature being kept at less than 5° C. After stirring for a further 30 minutes the mixture is filtered and the solvent is removed using a rotary evaporator. The resultant residue is re-filtered and the residue distilled in vacuo to yield N-methyl-hexanohydroxamic acid as an oil, b.p. 87°–90°/0.1 mm.

In a similar procedure to that described above butyryl chloride, decanoyl chloride and benzoyl chloride are used to prepare N-methyl-butyrohydroxamic acid, N-methyl-decanohydroxamic acid and N-methyl-benzohydroxamic acid.

Example 3: Formulation

The compounds of Examples 1 and 2 (13 mg) are dissolved in water (25 ml) and an appropriate aliquot is diluted with water to provide a suitable final concentration for administration. The procedure is carried out under sterile and pyrogen-free conditions to provide a composition suitable for injection or infusion.

Example 4: Activity of compounds as inhibitors of ferrylmyglobin

Ferrylmyoglobin was generated from metmyoglobin (MetMb) using hydrogen peroxide.

The metmyoglobin was purified for use by oxidizing 5 ml of a ca. 400 µM aqueous solution of metmyoglobin with a 741 µM aqueous solution of potassium ferricyanide in a 1:1 v/v ratio. This procedure converts the major part of any oxymyoglobin, which may be present in admixture with the metmyoglobin, to metmyoglobin. The mixture was then passed down a Sephadex G15-120 column to separate the potassium ferricyanide from the metmyoglobin, the latter being eluted first. By this procedure a stock solution of metmyoglobin was obtained with a concentration of about 110 µM and this was stored frozen in conveniently sized batches. The frozen solution was thawed at room temperature before use.

A stock solution of hydrogen peroxide of 1 mM concentration was prepared fresh every 4–5 hours and was stored in the fridge and wrapped in foil in an ice bucket on removal from the fridge in order to slow down decomposition.

The ferrylmyoglobin was generated in a final volume of aqueous solution of 1 ml containing myoglobin at a 20 µM concentration and hydrogen peroxide at a 25 µM concentration (1:1.25 molar ratio). This required the use of ca. 200 µl of the stock solution of myoglobin and 25 µl of the stock solution of hydrogen peroxide. The mixture was then incubated for 60 minutes. The percentage of ferrylmyoglobin (and ferrylmyoglobin radical) formed from the myoglobin by the action of the hydrogen peroxide was measured at intervals during the 60 minutes using Du65 and Du70 spectro-photometers by scanning the incubation mixture from 400–700 nm.

Using the incubation mixture containing only myoglobin and hydrogen peroxide as the control the effect was studied of incorporating into the mixture, with the myoglobin and prior to the addition of the hydrogen peroxide, either desferrioxamine or the compound (I), N-methylacetohydroxamic acid, at a concentration of 10 µM, 25 µM, 50 µM or 100 µM. In these experiments the total level of ferrylmyoglobin (including ferrylmyoglobin radical) was measured spectrophotometrically after time intervals of 0.5, 6.5, 15.5, 30.5 and 60 minutes after the addition of the hydrogen peroxide (no significant reaction was detected prior to the addition of the hydrogen peroxide).

Figure 2:
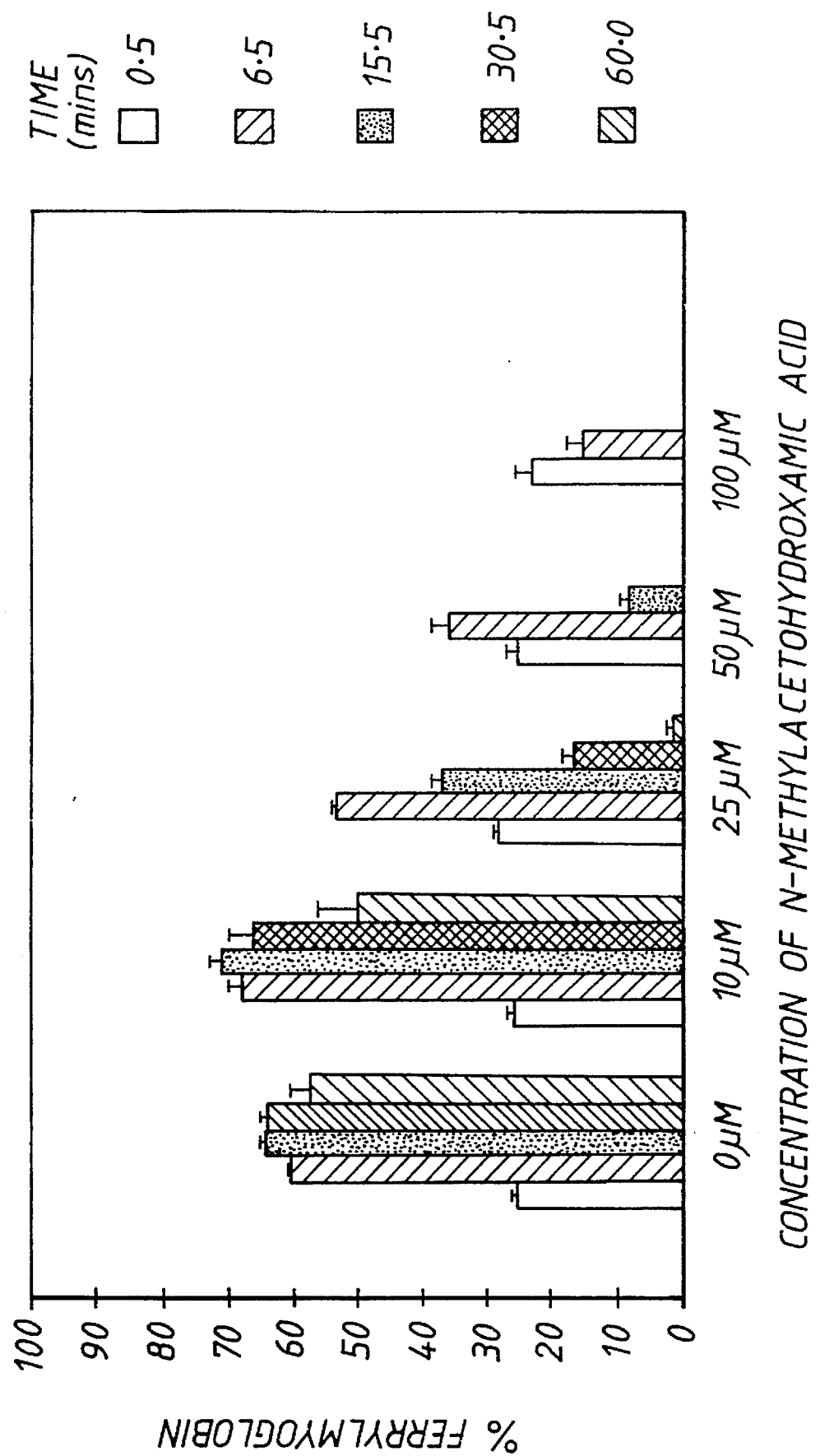

The effects of desferrioxamine and N-methylacetohydroxamic acid after these periods are illustrated in the form of histograms in FIGS. 1 and 2, respectively. At concentrations of 25 µM and higher the N-methylacetohydroxamic acid was found to be more effective than the desferrioxamine and to act more rapidly. At 50 µM and above N-methylacetohydroxamic acid was found to be very effective in suppressing peak ferrylmyoglobin formation so that by 100 µM the peak level had been suppressed to 30% and no ferrylmyoglobin was detectable after 10 minutes.

The above experiment was repeated with the following compounds at a concentration of 100 μM added at time zero (pre-formation of the free radicals) and in a separate experiment after 15 minutes (post-formation of the free radicals):— desferrioxamine
N-methyl-acetohydroxamic acid (NAMH)
N-methyl-benzohydroxamic acid (NBZMH)
N-methyl-butyrohydroxamic acid (NBMH)
N-methyl-hexanoyhydroxamic acid (NHMH).

The incubation mixture containing only myoglobin and hydrogen peroxide was used as a control.

Figure 3:
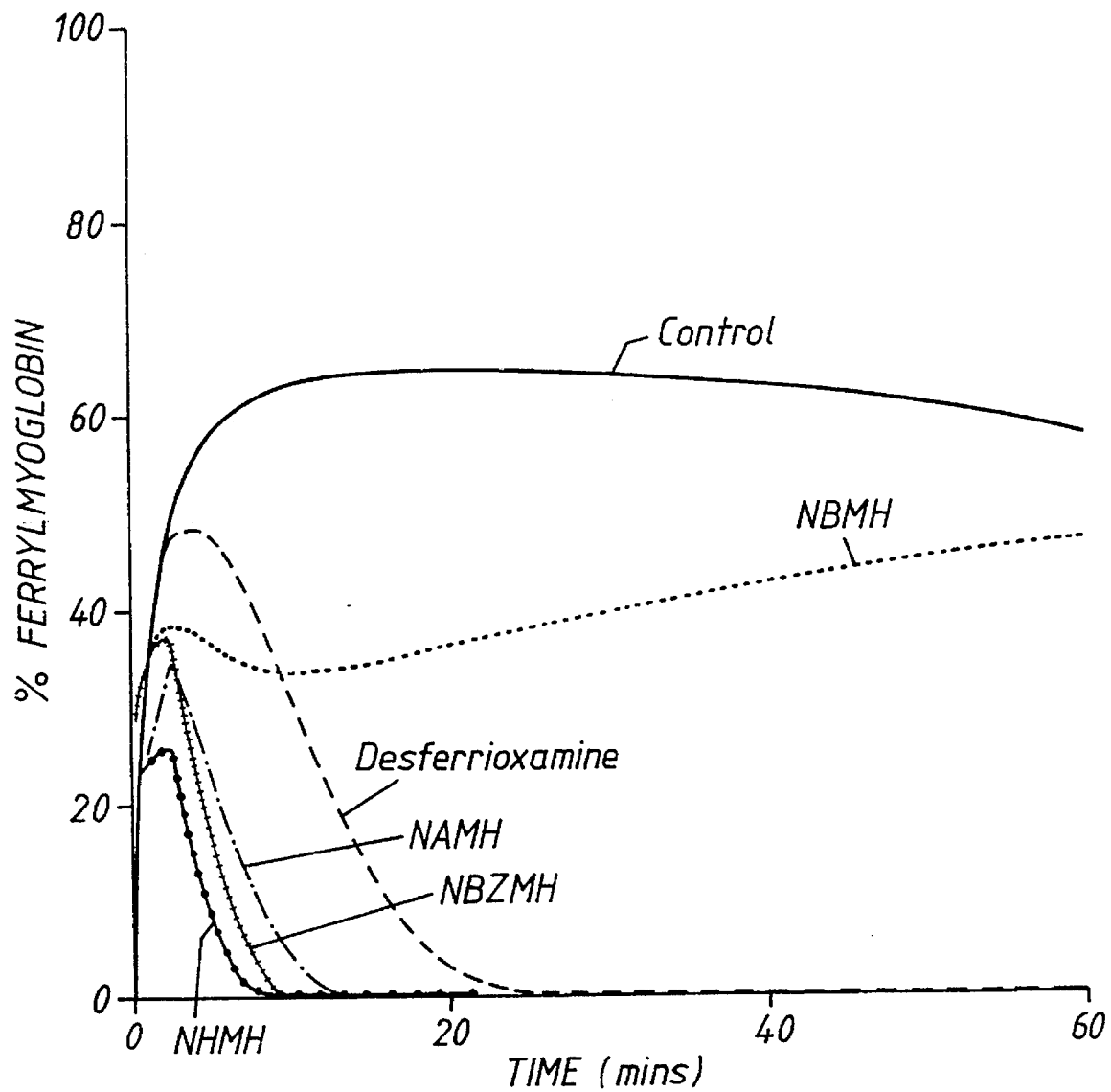
Figure 4:
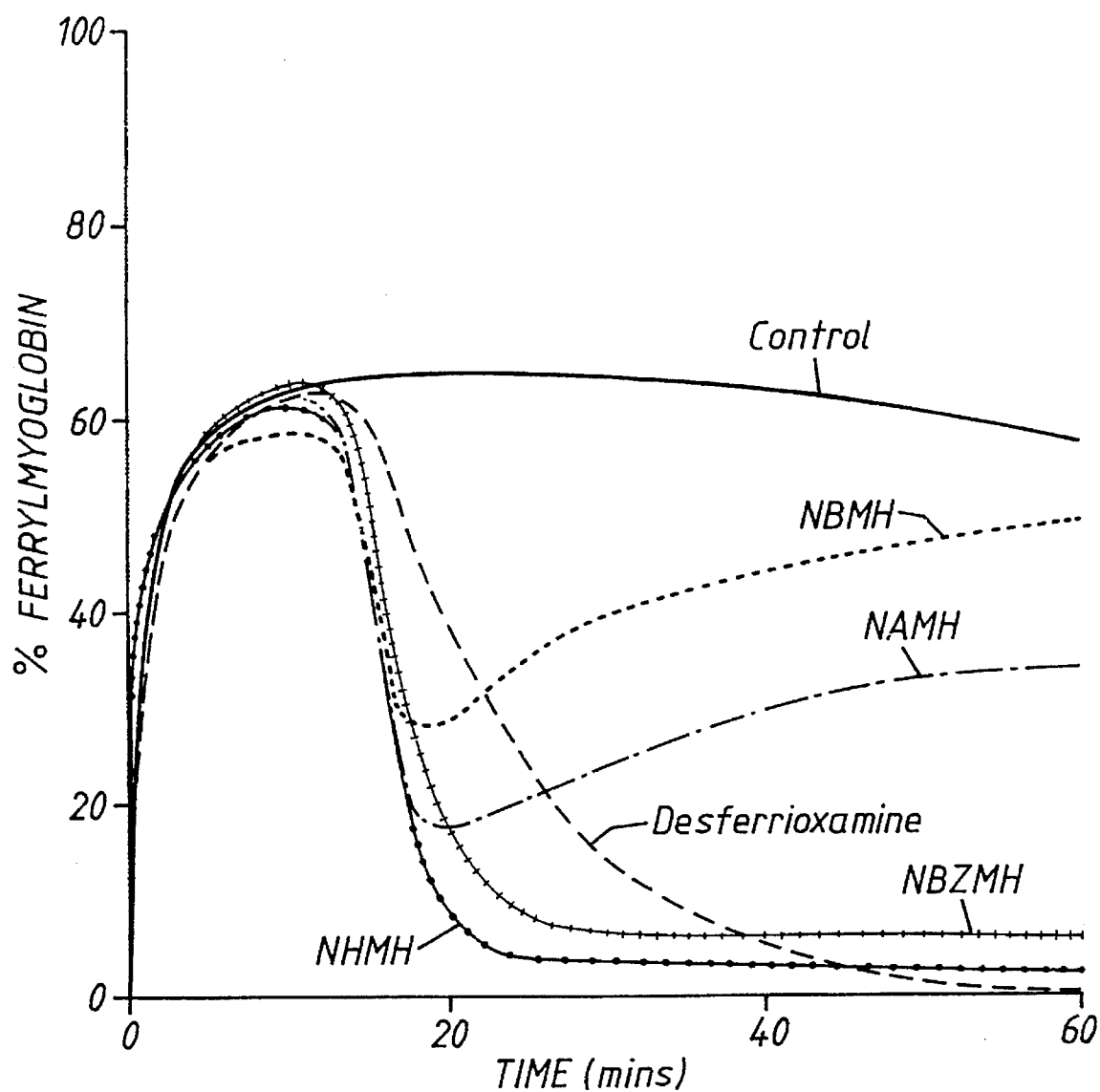

The results are shown in FIGS. 3 and 4 which show graphically the results of the two separate experiments.

In the case where inhibitors were added pre-radical formation, NHMH was the most effective compound, acting more rapidly than desferrioxamine. NAMH was also better than desferrioxamine. NBMH was not so effective.

The compounds were effective at reducing the ferrylmyoglobin concentration post-radical formation also. Both NBMH and NAMH showed an initial response, but did not totally reduce the amount of ferrylmyoglobin present. This observation is probably due to the fact that there is excess hydrogen peroxide present in the test system. This is able to react with any metmyoglobin formed by the initial reduction of the ferrylmyoglobin by the compounds and the compounds are not active enough at this concentration to prevent this reaction. NHMH was the most efficient of the compounds tested.

Example 5: Measurement of antioxidant ability in in vitro systems

The ability of the compounds of the invention to act as antioxidants protecting cell membranes against oxidative stress and to suppress the oxidation of low density lipoproteins (LDL) in in vitro systems was investigated.

LDL (final concentration protein 0.25 mg/ml) in phosphate buffer pH 7.4 was exposed to ferrylmyoglobin radicals by adding hydrogen peroxide (final concentration 25 μM) and the reaction initiated by the addition of 20 μM metmyoglobin. The extent of peroxidation was measured applying the thiobarbituric assay.

The inhibitory effect of the drugs was tested by incorporating the monohydroxamate compound (made up in buffer) final concentration as shown in Table 1 below prior to initiation of the oxidative stress mediated by the haem protein.

The efficacy of the drugs in inhibiting the propagation of peroxidation was effected by adding myoglobin alone to the preparation in the presence of the drug. The extent of lipid peroxidation was assessed as above. Results are expressed as a percentage of the level of peroxidation in the absence of the drug.

The results are shown in Table 1 below.

TABLE 1

INHIBITION OF INITIATION AND PROPAGATION OF LIPID PEROXIDATION BY CERTAIN HYDROXAMATE DRUGS

| DRUG | INITIATION (I)/ PROPAGATION (P) | INHIBITION OF LPO IN LDL5 (%) | INHIBITION OF LPO IN LDL6 (%) |
|---|---|---|---|
| NHMH | I | 93 | 91 |
| NHMH | P | 91 | 87 |
| NBMH | I | 97 | |
| NBMH | P | 87 | |
| DFO | I | 94 | |
| DFO | P | 69 | |

LDL Drug concentration 100 μM
LDL concentration 0.25 mg/ml
Membranes Drug conc. 50 μm
Membrane conc. 1.00 mg/ml NB Both concentrations expressed in terms of protein The oxidative status of LDL isolated from particular individuals will depend on their plasma antioxidant status. Thus those individuals, whose LDL contains limited levels of antioxidants endogenously, may have preformed lipid hydroperoxides in their LDL, whereas those whose endogenous antioxidant status is high would be less likely to have significant levels of preformed hydroperoxides in their blood. Hence, where preformed hydroperoxides are present, it is not necessary to generate radicals to initiate lipid peroxidation of the LDL, as it has already been initiated. In this case therefore we tested the drugs for their ability to suppress propagation of peroxidation induced by the haem protein.

LOOH + Haem protein ----≫ LO˙ ) these radicals can then
LOO˙ ) re-initiate peroxidation Thus, in this case, the compounds are shown to act as chain-breaking antioxidants, the monohydroxamates being more effective than desferrioxamine.

We claim:

1. A method for the treatment of a patient for the control of free radical induced damage arising from myocardial infraction or stroke, which method comprises the step of administering to said patient a therapeutically effective amount of a compound of formula I

in which R and R' are each separately selected from the group consisting of an aliphatic hydrocarbon group, an aryl group and an aliphatic hydrocarbon group substituted by an aryl group, or a physiologically acceptable salt of said compound.

2. A method according to claim 1, in which R and R' are each separately selected from an aliphatic hydrocarbon group of 1 to 12 carbon atoms.

3. A method according to claim 1, in which R and R' are each separately selected from the group consisting of methyl, ethyl, propyl, butyl, pentyl and hexyl groups.

4. A method according to claim 1, in which R' is methyl or ethyl.

5. A method according to claim 4, wherein the compound of formula (I) is selected from the group consisting of N-methyl-acetohydroxamic acid, N-ethyl-acetohydroxamic acid, N-methyl-propionohydroxamic acid, N-ethyl-propionohydroxamic acid, N-methyl-hexanohydroxamic acid and N-ethyl-hexanohydroxamic acid.

6. A method according to claim 5, wherein the compound of formula (I) is N-methyl-hexanohydroxamic acid.

7. A method for the treatment of a patient for control of free radical induced heart damage, which method comprises the step of administering to said patient a therapeutically effective amount of a compound of formula (I)

in which R and R' are each separately selected frown the group consisting of an aliphatic hydrocarbon group, an aryl group and an aliphatic hydrocarbon group substituted by an aryl group, or a physiologically acceptable salt of said compound.

8. A method for the treatment of a patient for control of free radical induced damage arising from reperfusion injury in organ transplantation, which method comprises the step of administering to said patient a therapeutically effective amount of a compound of formula (I)

in which R and R' are each separately selected from the group consisting of an aliphatic hydrocarbon group, an aryl group and an aliphatic hydrocarbon group substituted by an aryl group, or a physiologically acceptable salt of said compound.

9. A method for the treatment of a patient for controlling free radical induced organ tissue damage arising from sudden reperfusion of oxygen to said tissue, said method comprising the step of administering to said patient a therapeutically effective amount of a compound of formula I

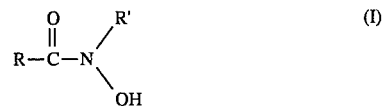

in which R and R' are each separately selected from the group consisting of an aliphatic hydrocarbon group, an aryl group and an aliphatic hydrocarbon group substituted by an aryl group, or a physiologically acceptable salt of said compound.

10. A method according to claim 9, wherein said organ is selected from the group consisting of the brain, the heart, the kidney and the liver.

* * * * *